US00PP36433P2

(12) United States Plant Patent
Johnson, Jr.

(10) Patent No.: US PP36,433 P2
(45) Date of Patent: Feb. 11, 2025

(54) ***MAHONIA* PLANT NAMED 'ALT 2'**

(50) Latin Name: *Mahonia eurybracteata*
Varietal Denomination: ALT 2

(71) Applicant: Ozzie W Johnson, Jr., Marietta, GA (US)

(72) Inventor: Ozzie W Johnson, Jr., Marietta, GA (US)

( * ) Notice: Subject to any disclaimer, the term of this patent is extended or adjusted under 35 U.S.C. 154(b) by 0 days.

(21) Appl. No.: 18/646,413

(22) Filed: Apr. 25, 2024

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ... A01H 5/12; A01H 5/02; A01H 5/00; A01H 6/00
See application file for complete search history.

(56) References Cited

PUBLICATIONS

Plant Development Services, Inc., *Mahonia* Silver Caress retrieved on Aug. 14, 2024 at https://plantdevelopment.com/introductions/mahonia-silver-caress/, 6 pp. (Year: 2024).*
Southern Living Plant Collection 2023, Technical Growing Guide for *Mahonia* Silver Caress, retrieved on Aug. 14, 2024 at https://plantdevelopment.com/wp-content/uploads/Mahonia_Silver_Caress.pdf, one page. (Year: 2023).*
USPTO Trademark Status & Document Retrieval, Reference No. 98448817 for Silver Caress, retrieved on Aug. 14, 2024 at https://tsdr.uspto.gov/#caseNumber=98448817&caseSearchType=US_APPLICATION&caseType=DEFAULT&searchType=statusSearch, 3 pp. (Year: 2024).*

* cited by examiner

*Primary Examiner* — June Hwu
(74) *Attorney, Agent, or Firm* — Cassandra Bright

(57) ABSTRACT

A new and distinct cultivar of *Mahonia* plant named 'ALT 2' is disclosed, characterized by narrow leaflets with a light greyed-green color, and a compact, dense habit. The new variety is a *Mahonia*, typically produced as an outdoor ornamental plant.

1 Drawing Sheet

Latin name of the genus and species: *Mahonia eurybracteata.*

Variety denomination: 'ALT 2'.

BACKGROUND OF THE INVENTION

The new cultivar is the product of cross pollination of the seed parent, the unpatented *Mahonia eurybracteata* 'Indianola Silver', with the unpatented *Mahonia eurybracteata* subsp. *ganpanensis*. The new cultivar 'ALT 2' was discovered by the inventor in 2009 at a home garden in Marietta, Georgia.

The first asexual reproduction was performed in 2009, at the same location in Marietta, Georgia using semi-softwood cuttings. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'ALT 2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALT 2'. These characteristics in combination distinguish 'ALT 2' as a new and distinct *Mahonia* cultivar:

1. Light grey-green colored foliage.
2. Dense plant structure.
3. Compact plant habit.
4. Increased cold hardiness.
5. Narrow leaflets.

PARENT COMPARISONS

Plants of the new cultivar 'ALT 2' are similar to the seed parent, the unpatented *Mahonia eurybracteata* 'Indianola Silver', in most horticultural characteristics. 'ALT 2', however, differs in the following:

1. Plants of the new variety are more compact than plants of the seed parent.
2. Foliage color of the new variety is lighter grey-green than the foliage color of the seed parent.
3. Leaflets of the new variety are narrower than leaflets of the seed parent.
4. Plants of the new variety are more cold hardy than plants of the seed parent.

Plants of the new cultivar 'ALT 2' are similar to the pollen parent, an unnamed, unpatented *Mahonia eurybracteata* subsp *ganpanensis*, in most horticultural characteristics. 'ALT 2', however, differs in the following:

1. Foliage color of the new variety is lighter grey-green than the foliage color of the pollen parent.
2. Growth habit of the new variety is more upright than the growth habit of the pollen parent.
3. Plants of the new variety are larger than plants of the pollen parent.

4. Plants of the new variety are more cold hardy than plants of the pollen parent.

COMMERCIAL COMPARISONS

Plants of the new cultivar 'ALT 2' can be compared to the commercial variety *Mahonica eurybracteata* 'Narihira', unpatented. Plants of these cultivars are similar in most horticultural characteristics, however, 'ALT 2' differs in the following:

1. Foliage color of the new variety is lighter grey-green than the foliage color of this comparator.
2. Growth habit of the new variety is more upright than the growth habit of this comparator.
3. Plants of the new variety are larger than plants of this comparator.
4. Plants of the new variety are more cold hardy than plants of this comparator.

Plants of the new cultivar 'ALT 2' can be compared to *Mahonia nervosa* 'Soft Caress', U.S. Plant Pat. No. 20,183. Plants of these cultivars are similar in most horticultural characteristics, however, 'ALT 2' differs in the following:

1. Foliage color of the new variety is lighter grey-green than the foliage color of this comparator.
2. Growth habit of the new variety is more upright than the growth habit of this comparator.
3. Plants of the new variety are larger than plants of this comparator.
4. Plants of the new variety are more cold hardy than plants of this comparator.

BRIEF DESCRIPTION OF THE PHOTOGRAPH

The accompanying photograph illustrates in full color a typical plant of 'ALT 2' grown in Marietta, Georgia. The plant is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ALT 2' plants grown outdoors in Marietta, Georgia. Plants are approximately 1.5 years old. Temperatures ranged from approximately 3° C. to 22° C. at night and 10° C. to 32° C. during the day. No artificial light, photoperiodic treatments were given to the plants. No chemical treatments were given to plants. Measurements and numerical values represent averages of typical plant types.

Botanical classification: *Mahonia eurybracteata* 'ALT 2'.

PROPAGATION

*Mahonia eurybracteata* 'ALT 2' has been reproduced through softwood cutting propagation.

PLANT

Growth habit: Broadly spreading, dense woody shrub.

Height: Approximately 70 cm for a 1.5 year old plant in a 5-gallon pot.

Plant spread: Approximately 60 cm.

Growth rate: Rapid.

Diameter of stem: Approximately 2.0 cm.

Length of stem: About 10 cm, then branching.

Color of stem: Mature stems near RHS Grey-Brown 197A mixed with Grey-Brown N199A and flushed Green 137C.

Texture of stem: Scaly and irregularly ridged.

Angle of stem: Lateral stems are straight and attached at angles between 45° to 90° from the main stem.

Internode length: About 6 cm to 8 cm.

FOLIAGE

Leaf:

*Arrangement*.—Compound, composed of 6 to 8-pairs of leaflets and a single apical leaflet.

*Quantity*.—Approximately 1 to 2 leaves per lateral branch.

*Length*.—Approximately 20 to 25 cm.

*Width*.—Approximately 8 to 13 cm.

Rachis:

*Length*.—Average range 8 to 14 cm.

*Diameter*.—3 mm.

*Texture*.—Glabrous.

*Color*.—Near RHS Green 137D.

Leaflets:

*Shape of blade*.—Elliptic.

*Length*.—Approximately 9.5 to 12.5 cm.

*Width*.—Approximately 2.2 cm at widest point.

*Apex*.—Acuminate.

*Base*.—Attenuate.

*Margin*.—10 to 12 moderately sharp serrations per leaflet.

*Attachment*.—Sessile.

*Texture of top surface*.—Glabrous.

*Texture of bottom surface*.—Glabrous.

*Appearance upper surface*.—Matte.

*Appearance lower surface*.—Matte.

*Aspect*.—Flat to weakly arched.

*Color*.—Young foliage upper side: Near RHS Green 138B lightly flushed Greyed-Green 194C. Young foliage under side: Near RHS Green 138C. Mature foliage upper side: Near RHS Green 137A. Mature foliage under side: Near RHS Green 138B heavily flushed Greyed-Green 194C.

*Venation*.—Type: Pinnate. Venation color upper side: Near RHS Green 138C. Venation color under side: Near RHS Green 138C.

*Petiole*.—Length: Average 5.5 cm. Diameter: Approximately 3 mm. Color: Near RHS Green 138A. Texture: Glabrous.

FLOWER

Natural flowering season: Around January to February.

Inflorescence and flower type and habit: Fascicled raceme composed of perfect, upwardly cupped flowers.

Flowers per inflorescence: Average range 40 to 60.

Inflorescence size:

*Diameter*.—About 3 cm.

*Height*.—Average range from about 9 cm to 15 cm.

Flower longevity on plant: About 10 to 15 days, self-cleaning.

Bud:

*Shape*.—Conical.

*Length*.—About 11 mm.

*Diameter*.—About 9 mm.
*Color*.—Near RHS Yellow-Green 144C.

Flower size:
*Diameter*.—9 mm.
*Height*.—3 cm.

Petals:
*Arrangement*.—Whorled.
*Quantity*.—6.
*Length*.—3 cm.
*Diameter*.—2 mm.
*Texture*.—Glabrous.
*Apex*.—Retuse.
*Base*.—Truncate.
*Margin*.—Entire.
*Color*.—When opening: Upper surface: Near RHS Yellow 3C. Lower surface: Near RHS Yellow 3B. Fully opened: Upper surface: Near RHS Yellow 7B. Lower surface: Near RHS Yellow 4A.

Corolla: Cup-shaped, approximately 3 mm in diameter, 5 mm in height.

Sepals:
*Quantity per flower*.—6.
*Shape*.—Ovate.
*Length*.—4 mm.
*Width*.—3 mm.
*Apex*.—Acute.
*Base*.—Truncate.
*Margin*.—Entire.
*Texture*.—Glabrous.
*Color*.—Near RHS Yellow-Green 154C, upper and lower surfaces.

Peduncle:
*Length*.—Average range 8 to 14 cm.
*Diameter*.—3 mm.
*Color*.—Near RHS Yellow-Green N144A.
*Strength*.—Moderately strong.
*Angle*.—45° to 90° angle from stem.

Pedicel:
*Length*.—About 3 mm.
*Diameter*.—About 1 mm.
*Color*.—Near RHS Yellow-Green 144B.

Fragrance: Faint sweet scent.

REPRODUCTIVE ORGANS

Stamens:
*Number*.—6.
*Filament length*.—11 mm.
*Filament color*.—Near RHS Yellow-Green 150D.

Anthers:
*Shape*.—Oblong.
*Length*.—2 mm.
*Color*.—Near RHS Yellow-Green 154D.

Pollen:
*Color*.—Near RHS Yellow-Green 154D.
*Quantity*.—Moderate.

Pistil:
*Quantity*.—1.
*Length*.—3 mm.
*Style*.—Reduced, indistinguishable.
*Ovary*.—Diameter: 1 mm. Color: Near RHS Yellow-Green 154B.

OTHER CHARACTERISTICS

Fruit: Ovoid berry, approximately 7 mm in length and 4 mm diameter. Colored near RHS Violet-Blue 98A.

Seed: 1 to 5 per fruit. Flattened sphere, 4 mm long, 3 mm diameter. Colored near RHS Greyed-Orange 164D.

Disease/pest resistance: Neither resistance nor susceptibility to the normal diseases and pests of *Mahonia* has been observed.

Temperature tolerance: USDA Zones 6-9.

Drought tolerance: Tolerance for drought not tested.

What is claimed is:

1. A new and distinct cultivar of *Mahonia* plant named 'ALT 2' as herein illustrated and described.

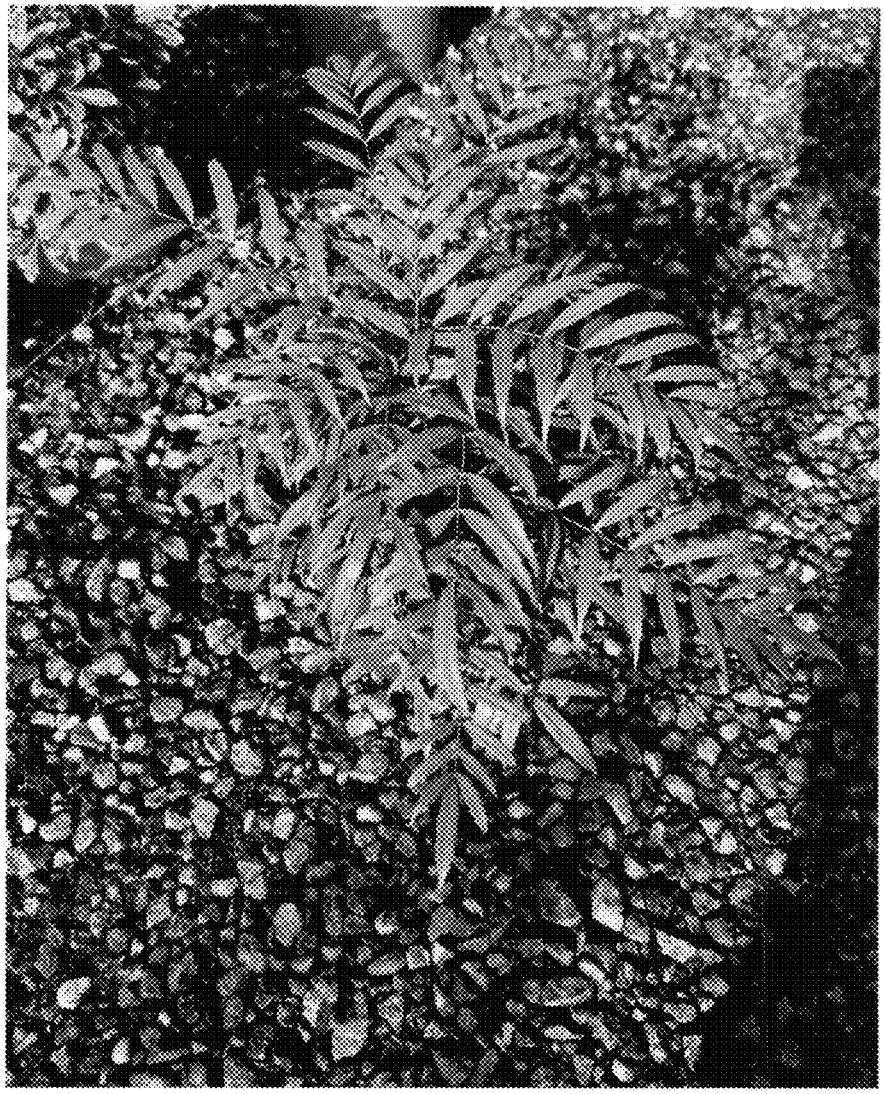

* * * * *